US008663331B2

(12) United States Patent
McClellan, III et al.

(10) Patent No.: US 8,663,331 B2
(45) Date of Patent: Mar. 4, 2014

(54) MAXIMUM SUPPORT TLIF IMPLANT

(75) Inventors: John W. McClellan, III, Omaha, NE (US); Matthew P. McClellan, Omaha, NE (US)

(73) Assignee: Custom Spine, Inc., Parsippany, NJ (US)

( * ) Notice: Subject to any disclaimer, the term of this patent is extended or adjusted under 35 U.S.C. 154(b) by 1686 days.

(21) Appl. No.: 11/947,884

(22) Filed: Nov. 30, 2007

(65) Prior Publication Data

US 2009/0143859 A1    Jun. 4, 2009

(51) Int. Cl.
*A61F 2/44*    (2006.01)

(52) U.S. Cl.
USPC .................... 623/17.16; 623/17.11

(58) Field of Classification Search
USPC ............................. 623/17.11, 17.16
See application file for complete search history.

(56) References Cited

U.S. PATENT DOCUMENTS

| 6,193,757 | B1 | 2/2001 | Foley et al. |
| 6,245,108 | B1 * | 6/2001 | Biscup ...................... 623/17.11 |
| 7,018,413 | B2 | 3/2006 | Krüger |
| 2004/0127990 | A1 * | 7/2004 | Bartish et al. .............. 623/17.11 |
| 2005/0119747 | A1 * | 6/2005 | Monterumici et al. .... 623/17.11 |
| 2006/0229725 | A1 * | 10/2006 | Lechmann et al. ........ 623/17.11 |
| 2007/0067035 | A1 | 3/2007 | Falahee |
| 2007/0260314 | A1 | 11/2007 | Biyani |

* cited by examiner

*Primary Examiner* — Christian Sevilla
(74) *Attorney, Agent, or Firm* — Rahman LLC

(57) ABSTRACT

A transforaminal lumbar interbody fusion (TLIF) implant to be placed in an intervertebral space includes a front member and a back member. The front member includes a first end having a hinge, a second end, a pair of lateral portions, a top wall and a bottom wall, an opening configured through the pair of lateral portions and a plurality of openings in each of the top wall and the bottom wall. The back member includes a first end having an arcuately-shaped attachment head comprising a receptor dimensioned and configured to accommodate the hinge of the front member, a second end, a pair of lateral portions, a top wall, a bottom wall and an opening configured through the pair of lateral portions. The top wall and the bottom wall of the back member further comprise a plurality of openings.

20 Claims, 7 Drawing Sheets

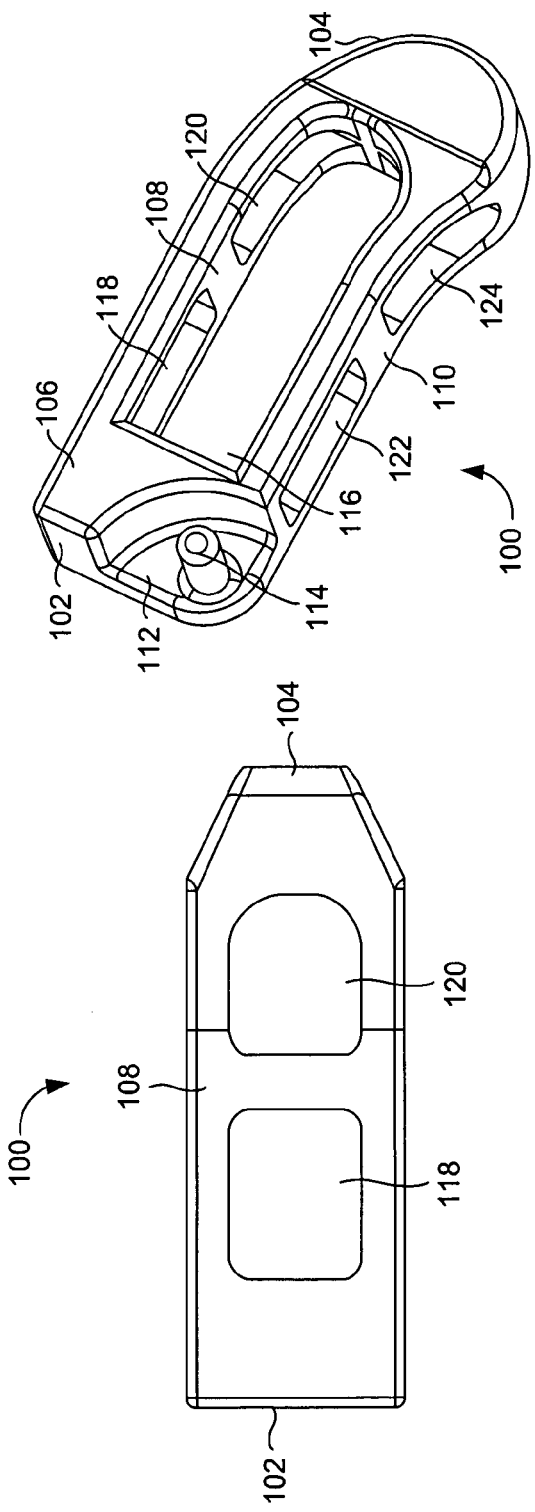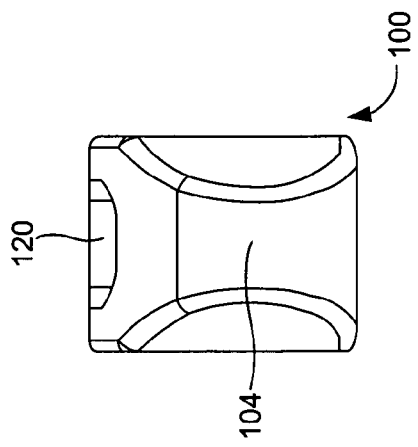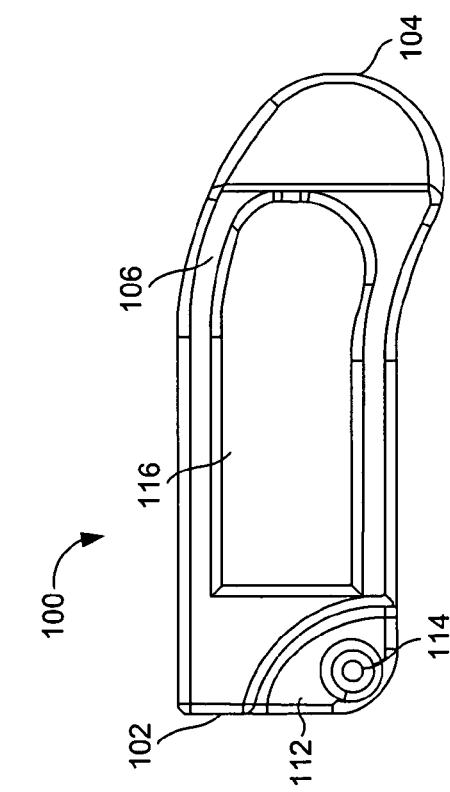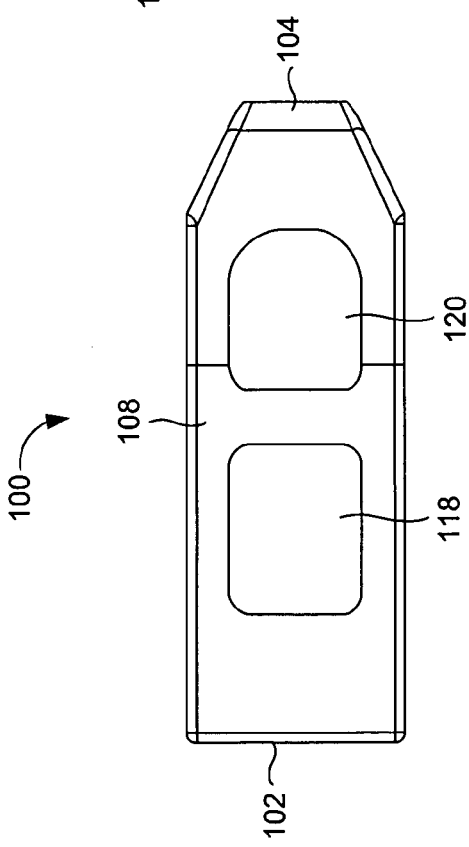

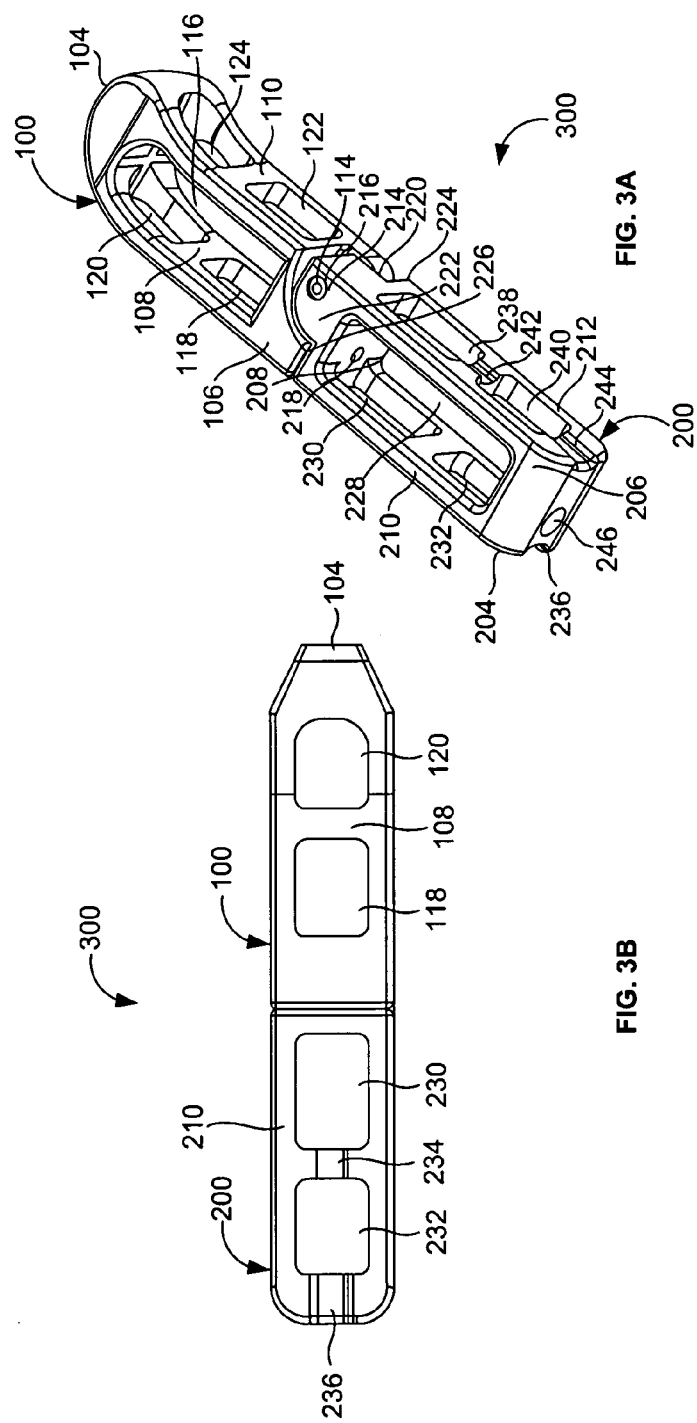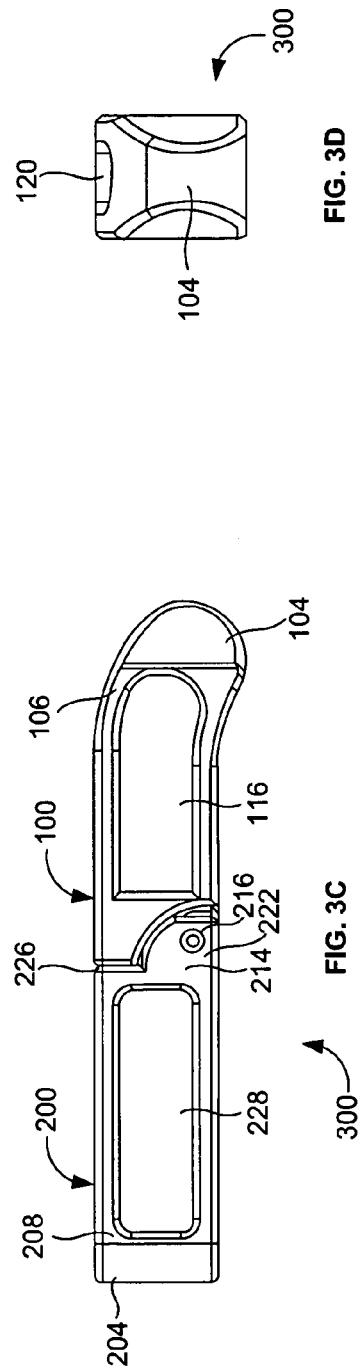

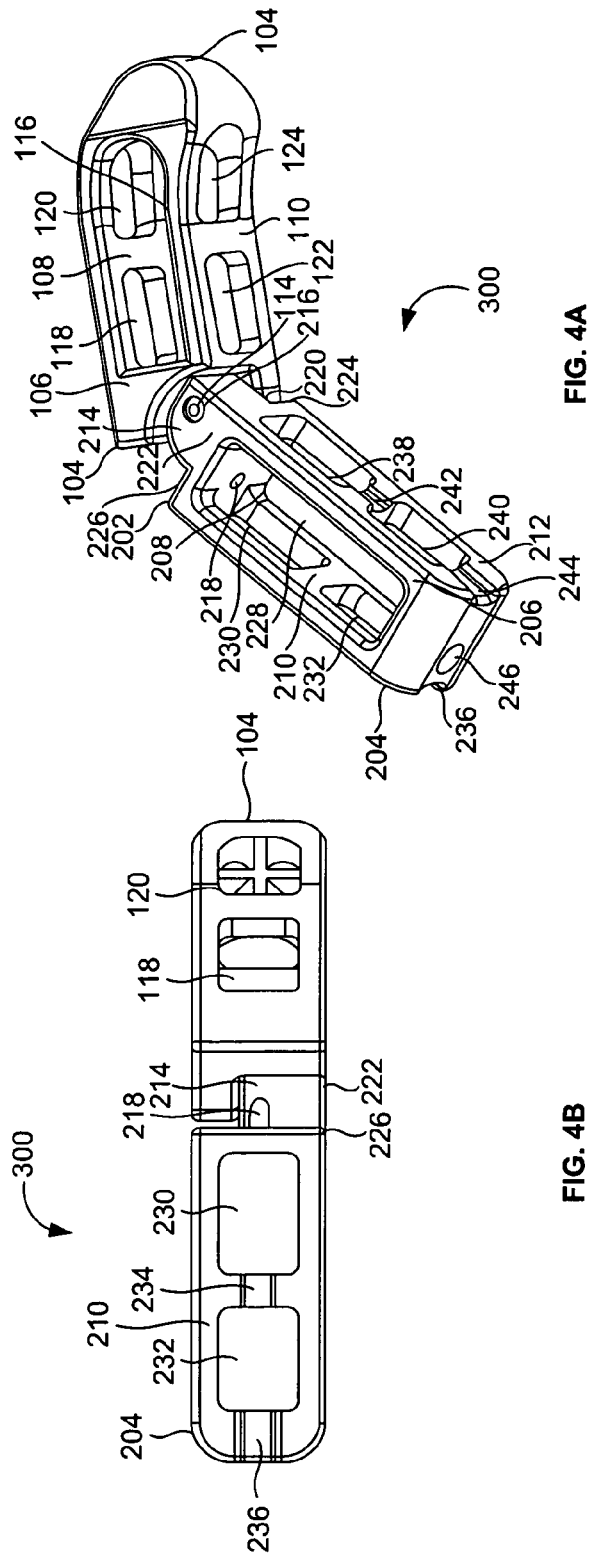
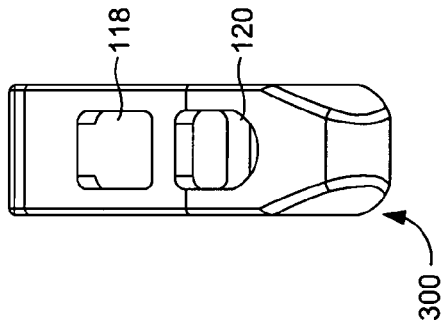
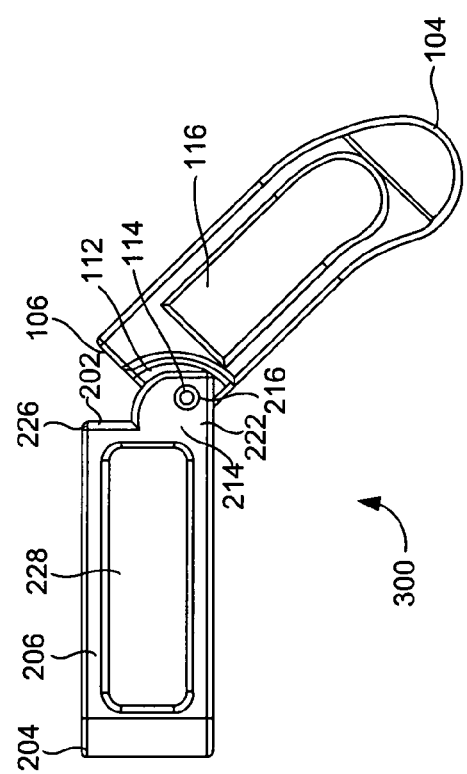
FIG. 4A
FIG. 4D
FIG. 4B
FIG. 4C

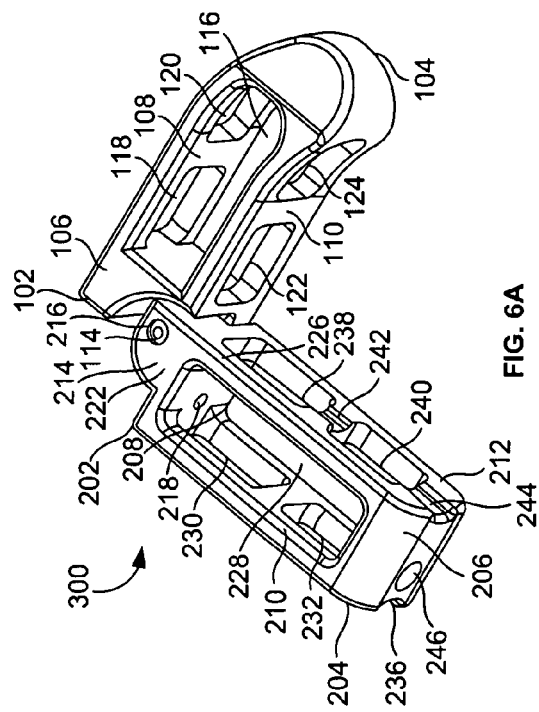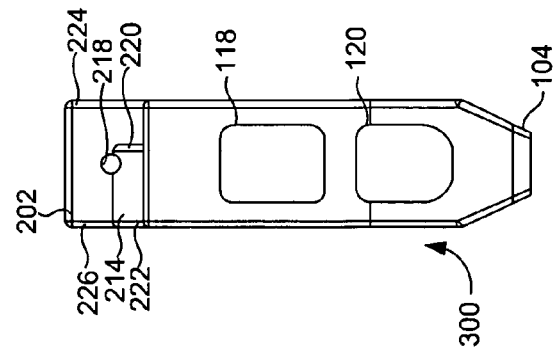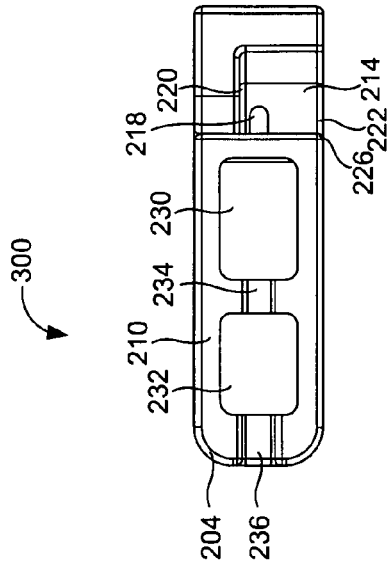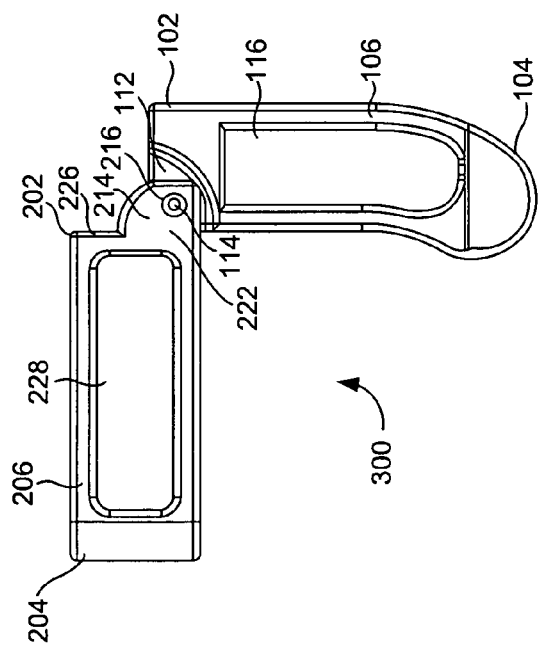

MAXIMUM SUPPORT TLIF IMPLANT

BACKGROUND

1. Technical Field

The embodiments herein generally relate to medical devices, and, more particularly, to a maximum support TLIF implant used during orthopedic surgeries.

2. Description of the Related Art

Intervertebral discs, which occupy one fourth of the human vertebral column's total length, are fibrocartilaginous cushions between two adjacent vertebrae. The discs act as shock absorbers and protect the vertebrae, brain, and nerves. The discs permit some limited vertebral extension and flexion motions as well as maintain the stability of the vertebral segments while absorbing external forces. Due to aging and some injuries, the inteverterbral discs start degenerating leading to degenerative disc disease. This causes chronic back pain and can gradually lead to spinal stenosis in which the spinal canal becomes narrower and puts pressure on the spinal cord and nerves. Spinal fusions are common procedures used for fusing and stabilizing the vertebrae.

Transforaminal lumbar interbody fusion (TLIF), one type of spinal fusion, is generally performed through the posterior part of the spine. The affected and degenearated disc is removed from the intervertebral space and an interbody fusion spacer is inserted to maintain the intervertebral space height and take pressure off from the nerves. Bone graft is then placed into the interbody space which helps in new bone formation. Traditional interbody spacers are available in various configurations. Amongst them, one-piece devices are designed for simple insertion. They provide a fixed amount of surface area. Other devices are single piece and expandable. The expandable devices are inserted and then expanded using different techniques. These devices however, do not offer significant change in direct endplate support. Typically, the expandable devices offer the same direct endplate support whether in an expanded or non-expanded position. Those skilled in the art have noted that surface area is important to controlling postoperative pain and achieving successful fusion. Accordingly, there remains a need for a new TLIF implant cage to provide maximum surface area with excellent pain control and improved stability.

SUMMARY

In view of the foregoing, an embodiment herein provides a TLIF implant to be placed in an intervertebral space. The TLIF implant includes a front member and a back member pivotally attached to the front member. The front member further includes a first end having a hinge, a second end having a tapered configuration, a pair of lateral portions, a top wall and a bottom wall. The second end is positioned opposite to the first end. The pair of lateral portions is attached to each of the first end and the second end. The top wall and the bottom wall are attached to each of the first end, the second end, and the pair of lateral portions. The bottom wall is positioned opposite to the top wall. In addition, the front member includes an opening configured through the pair of lateral portions and a plurality of openings in each of the top wall and the bottom wall.

The back member includes a first end, a second end positioned opposite to the first end, a pair of lateral portions, a top wall, a bottom wall and an opening configured through the pair of lateral portions. The first end further includes an arcuately-shaped attachment head comprising a receptor. The receptor is dimensioned and configured to accommodate the hinge of the front member. The second end has a tapered configuration and a tip of the tapered configuration comprises a hole recess. The pair of lateral portions is attached to each of the first end and the second end of the back member. The top wall and the bottom wall are attached to each of the first end, the second end, and the pair of lateral portions of the back member. The bottom wall is positioned opposite to the top wall. The top wall and the bottom wall further comprise a plurality of openings and a plurality of slots. The plurality of slots comprises a top pair of slots in the top wall and a bottom pair of slots in the bottom wall. A rear slot of the top pair of slots and a rear slot of the bottom pair of slots merge. The first end of the back member comprises a hole recess adjacent to the attachment head and aligned with the hole recess of the second end. The plurality of slots is adapted to accommodate impactions to turn the TLIF implant.

In another aspect, a device for providing intervertebral support includes a first member and a second member pivotally attached to the first member. The first member further includes a first end comprising a cylindrical hinge, a curved second end, a pair of lateral portions, top wall and a bottom wall. The curved second end includes a tapered configuration and is positioned opposite to the first end. The pair of lateral portions is attached to the first end and the second end. The top wall and the bottom wall are attached to each of the first end, the second end, and the pair of lateral portions. The bottom wall is positioned opposite to the top wall. One of the lateral portions comprises an arcuately-shaped cut out region comprising the hinge. The first member further includes an opening configured through the pair of lateral portions. A length of the opening is at least equal to half of an overall length of the first member and the opening is adjacent to the arcuately-shaped cut out region. The top wall and the bottom wall include a plurality of elongated openings. The openings in the top wall are aligned with the openings in the bottom wall.

The second member comprises a first end, a second end, a first lateral portion, a second lateral portion, a top wall, a bottom wall and an opening configured through the first lateral portion and the second lateral portion. The second end has a tapered configuration and is positioned opposite to the first end. The second lateral portion is positioned opposite to the first lateral portion. The first lateral portion and the second lateral portion are attached to each of the first end and second end. The top wall and the bottom wall are attached to each of the first end, the second end, the first lateral portion and the second lateral portion. The bottom wall is positioned opposite to the top wall. The top wall and the bottom wall include a plurality of openings and a plurality of slots. The openings in the top wall are aligned with the openings in the bottom wall. The plurality of slots comprises a top pair of slots in the top wall and a bottom pair of slots in the bottom wall. A rear slot of the top pair of slots and a rear slot of the bottom pair of slots merge. The plurality of slots is adapted to accommodate impactions to turn the device.

The first end of the second member further includes an arcuately-shaped attachment head corresponding to the arcuately-shaped cut out region of the first member. The attachment head comprises a receptor dimensioned and configured to pivotally attach to the hinge of the first member. A first lateral side of the attachment head is offset from an edge of the first lateral portion and a second lateral side of the attachment head is planar with an edge of the second lateral portion. A tip of the tapered configuration of the second end comprises a hole recess positioned parallel to a longitudinal axis of the second member. The first end comprises a hole recess adjacent to the attachment head and aligned with the hole recess of the second end.

In yet another aspect, a method of performing a surgical procedure includes inserting a TLIF implant into an intervertebral space in a first position, adjusting a position of the TLIF implant so that a front member is pivotally tilted with respect to a back member to form a second position, adjusting the position of the TLIF implant so that the front member is pivotally tilted with respect to the back member to form a third position, adjusting the position of the TLIF implant so that the front member is pivotally tilted with respect to the back member to form a fourth position, inserting an inserter tool through a second hole recess in a tip of a tapered configuration of a second end of the back member, inserting the inserter tool through a first hole recess in a first end of the back member, pushing the front member in order to cause the front member to pivot with respect to the back member, and setting the TLIF implant in the intervertebral space in the fourth position.

The first end of the front member comprises a hinge. The second end has a tapered configuration and is positioned opposite to the first end. The front member further includes a pair of lateral portions, an opening configured through the pair of lateral portions, a top wall, a bottom wall and a plurality of openings in each of the top wall and the bottom wall. The pair of lateral portions is attached to each of the first end and the second end. The top wall and the bottom wall are attached to each of the first end, the second end, and the pair of lateral portions. The bottom wall is positioned opposite to the top wall.

The back member is pivotally attached to the front member. The back member further comprises a first end, the second end, a pair of lateral portions, a top wall, a bottom wall and an opening configured through the pair of lateral portions. The second end has the tapered configuration and is positioned opposite to the first end. The pair of lateral portions is attached to each of the first end and second end. The top wall and the bottom wall are attached to each of the first end, the second end and the pair of lateral portions. The bottom wall is positioned opposite to the top wall. The top wall and the bottom wall include a plurality of openings. The first end of the back member further includes an arcuately-shaped attachment head. The attachment head comprises a receptor dimensioned and configured to pivotally attach to the hinge of the front member. The tip of the tapered configuration of the second end comprises the second hole recess positioned parallel to a longitudinal axis of the back member. The first end comprises the first hole recess adjacent to the attachment head and aligned with the second hole recess of the second end.

The first position is a position in which the front member is pivoted with respect to the back member to form an angle of 0 degrees. The second position is a position in which the front member is pivoted with respect to the back member to form an angle of 45 degrees. The third position is a position in which the front member is pivoted with respect to the back member to form an angle of 115 degrees. The fourth position is a position in which the front member is pivoted with respect to the back member to form an angle of 90 degrees.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 1A through 1D illustrate a perspective view, a top view, a side view, and an end view, respectively, of a front member of a TLIF implant according to an embodiment herein;

FIGS. 3A through 3D illustrate a perspective view, a top view, a side view, and a back view, respectively, of an assembled TLIF implant cage in a first position according to an embodiment herein;

FIGS. 4A through 4D illustrate a perspective view, a top view, a side view, and a back view, respectively, of the TLIF implant cage of FIG. 3A through 3D in a second position according to an embodiment herein;

FIGS. 6A through 6D illustrate a perspective view, a top view, a side view, and a back view, respectively, of the TLIF implant cage of FIG. 3A through 3D in a fourth position according to an embodiment herein.

DETAILED DESCRIPTION OF PREFERRED EMBODIMENTS

Figure 2A:
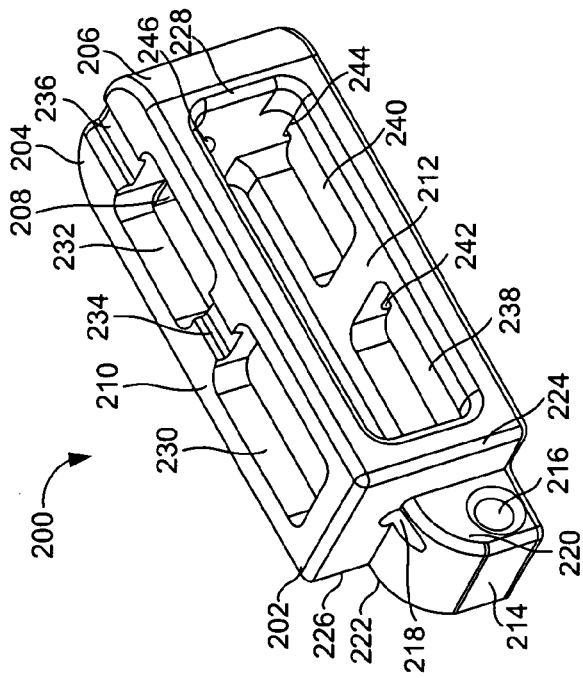
FIGS. 2A through 2D illustrate a perspective view, a top view, a side view, and an end view, respectively, of a back member of a TLIF implant according to an embodiment herein.
Figure 2D:
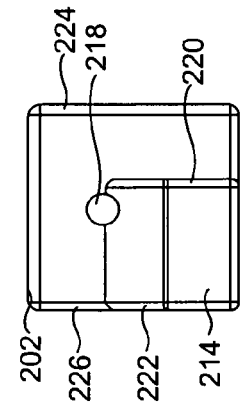
Figure 2B:
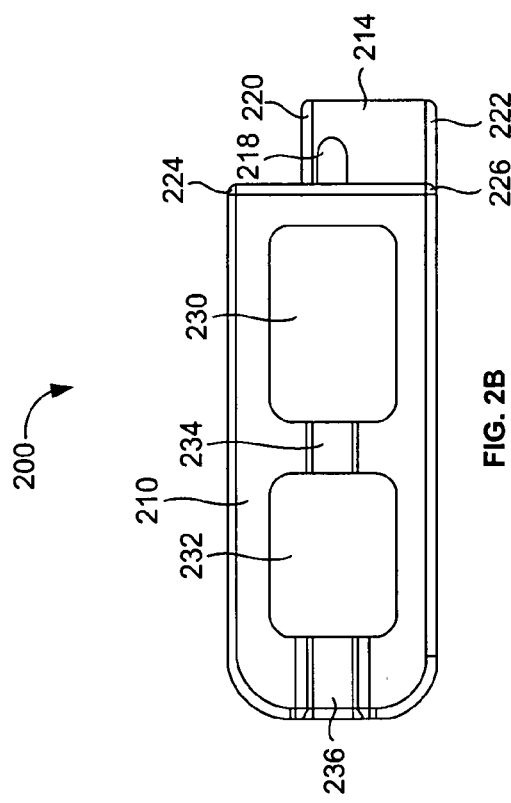
Figure 2C:
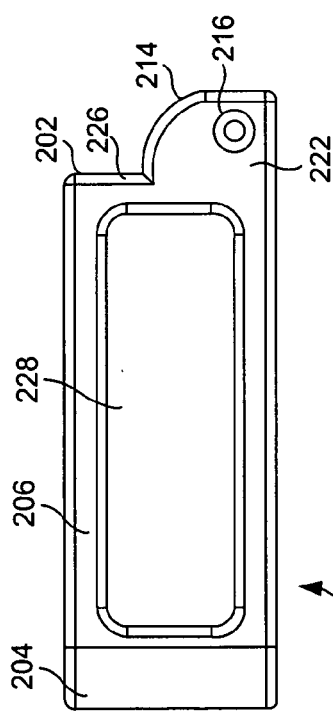
Figure 5A:
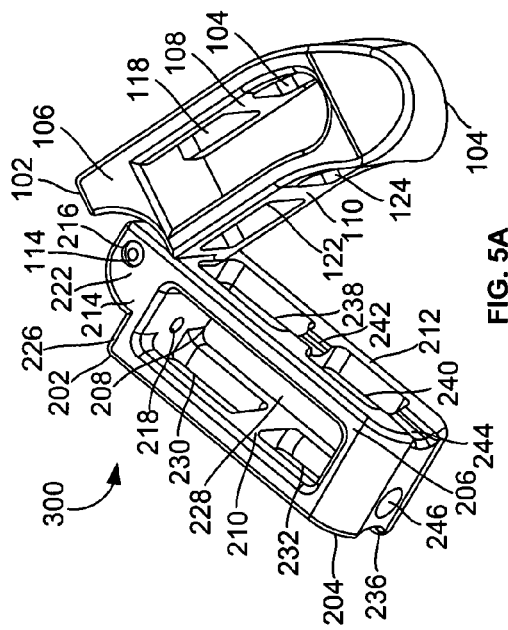
FIGS. 5A through 5D illustrate a perspective view, a top view, a side view, and a back view, respectively, of the TLIF implant cage of FIG. 3A through 3D in a third position according to an embodiment herein.
Figure 5D:
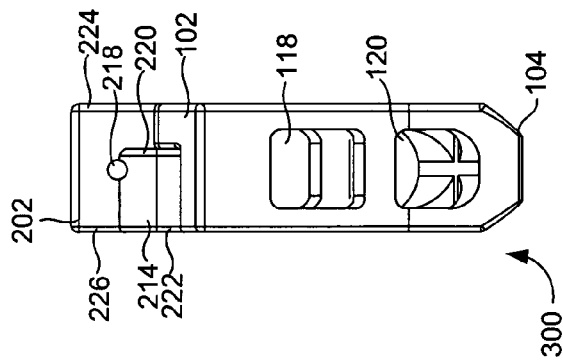
Figure 5B:
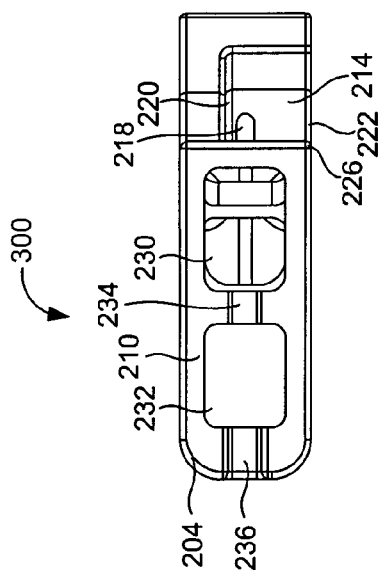
Figure 5C:
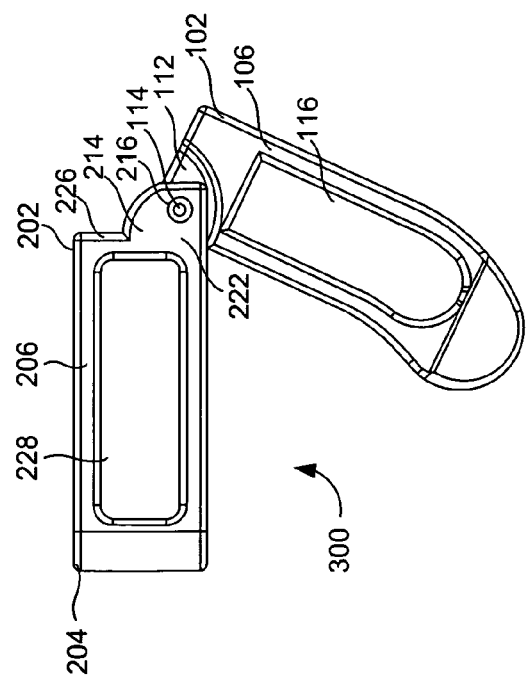

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new TLIF implant cage to provide maximum surface area with excellent pain control and improved stability. The embodiments herein achieve this by providing a TLIF implant to be placed in an intervertebral space, the TLIF implant including a front member and a back member pivotally attached to the front member. The front member includes a first end having a hinge, a second end positioned opposite to the first end, a pair of lateral portions attached to each of the first end and the second end, a top wall, and a bottom wall. The back member includes a first end having an arcuately-shaped attachment head and a receptor dimensioned and configured to accommodate the hinge of the front member, a second end positioned opposite to the first end, a first lateral portion, a second lateral portion, a top wall and a bottom wall. Referring now to the drawings, and more particularly to FIGS. 1A through 7, where similar reference characters denote corresponding features consistently throughout the figures, there are shown preferred embodiments.

FIGS. 1A through 1D illustrate a perspective view, a top view, a side view, and an end view, respectively, of a front member 100 of a TLIF implant cage 300 (of FIGS. 3A through 6D) according to an embodiment herein. The front member 100 includes a first end 102, a second curved end 104, a pair of lateral portions 106, a top wall 108, and a bottom wall 110. The second curved end 104 is positioned opposite to the first end 102 and has a tapered configuration. The pair of lateral portions 106 is attached to each of the first end 102 and the second curved end 104. The top wall 108 and the bottom wall 110 are attached to each of the first end 102, the second end 104, and the pair of lateral portions 106. The bottom wall 110 is positioned opposite to the top wall 108. The top wall 108 and the bottom wall 110 are at a first side and a second side, respectively, of the pair of lateral portions 106.

One of the pair of lateral portions 106 further includes an arcuately-shaped cut out region 112 having a cylindrical hinge 114. In addition, the front member 100 includes an opening 116 which is configured through the pair of lateral portions 106. The opening 116 is positioned adjacent to the cut out region 112. The length of the opening 116 is at least equal to half of an overall length of said front member 100. The top wall 108 and the bottom wall 110 further include a plurality of elongated openings 118, 120, 122, 124. The openings 118, 120 in the top wall 108 are aligned with the openings 122, 124 in the bottom wall 110.

FIGS. 2A through 2D illustrate a perspective view, a top view, a side view, and an end view, respectively, of a back member 200 of a TLIF implant cage 300 (of FIGS. 3A through 6D) according to an embodiment herein. The back member 200 includes a first end 202, a second end 204, a first lateral portion 206, a second lateral portion 208, a top wall 210, and a bottom wall 212. The second end 204 is tapered in configuration. The second end 204 is positioned opposite to the first end 202. The first lateral portion 206 and the second lateral portion 208 are attached to the first end 202 and the second end 204. The top wall 210 and the bottom wall 212 are attached to each of the first end 202, the second end 204, the first lateral portion, and the second lateral portion 208. The top wall 210 and the bottom wall 212 are adjacent to the first lateral portion 206.

The first end 202 further includes an arcuately-shaped attachment head 214 comprising a receptor 216, a first hole recess 218, a first lateral side 220 and a second lateral side 222. The first hole recess 218 is positioned adjacent to the attachment head 214 and extends through to the inside of the back member 200. Moreover, the first hole recess 218 is positioned parallel to a longitudinal axis of the back member 200. The first lateral portion 206 includes an edge 224 and the second lateral portion 208 includes an edge 226. The first lateral side 220 of the attachment head 214 is offset from the edge 224 of the first lateral portion 206, and the second lateral side 222 of the attachment head 214 is planar with the edge 226 of the second lateral portion 208.

In addition, the back member 200 includes an opening 228 configured through the first lateral portion 206 and the second lateral portion 208. The top wall 210 further includes two openings 230, 232 and a top pair of slots 234, 236. The bottom wall 212 further includes two openings 238, 240 and bottom pair of slots 242, 244. The rear slot 236 of the top pair of slots of the top wall 208 and the rear slot 244 of the bottom pair of slots of the bottom wall 210 are merged. In addition, the back member 200 includes a second hole recess 246, which is present on a tip of the tapered configuration of the second end 204. The second hole recess 246 is positioned parallel to a longitudinal axis of the back member 200. The first hole recess 218 is preferably aligned with the second hole recess 246.

FIGS. 3A through 3D illustrate a perspective view, a top view, a side view, and a back view, respectively, of a TLIF implant cage 300 having the front member 100 (of FIGS. 1A through 1D) and the back member 200 (of FIGS. 2A through 2D) in a first position according to an embodiment herein. The hole recesses 218, 246 are configured to allow an inserter tool (not shown) to be inserted into the back member 200 to urge the TLIF implant cage 300 into position in an intervertebral space (not shown) of the human spine by pushing the first end 102 of the front member 100 so that the front member 100 pivots with respect to the back member 200. Accordingly, the back member 200 is pivotally attached to the front member 100 due to the engagement of the front member 100 by an inserter tool (not shown), which may be any suitable type of inserter tool that preferably includes an elongated shaft portion capable of reaching and engaging the front member 100.

The attachment head 214 of the back member 200 is connected to the cylindrical hinge 114 on the cut out 112 of the front member 100. The receptor 216 of the attachment head 214 accommodates the cylindrical hinge 114 of the cut out 112. Preferably, the cylindrical hinge 114 is press fit into the receptor 216 but has a sufficient radial tolerance to allow the back member 200 to pivot with respect to the front member 100. The cut out 112 that is coupled with the attachment head 214 may act as a support and enable the front member 100 to rotate at different angles with respect to the back member 200. In the first position, both the front member 100 and the back member 200 remain in a straightened position with a zero degree angle between the first end 102 of the first member 100 and the first end 202 of the back member 200.

The openings 116, 118, 120, 122, 124 of the front member 100 and the openings 228, 230, 232, 238, 240 of the back member 200 may be configured to receive bone graft material which helps in further bone formation. The plurality of slots 234, 236, 242, 244 is configured to accommodate impactions to turn the TLIF implant 300 inside the intervertebral space. The TLIF implant 300 may be inserted into the intervertebral space in the first position.

FIGS. 4A through 4D illustrate a perspective view, a top view, a side view, and a back view, respectively, of the TLIF implant cage 300 (of FIGS. 3A through 3D) in a second position according to an embodiment herein. The front member 100 is tilted upon its cylindrical hinge 114 to form an angle of 45 degrees between the first end 102 of the first member 100 and the first end 202 of the back member 200.

FIGS. 5A through 5D illustrate a perspective view, a top view, a side view, and a back view, respectively, of the TLIF implant cage 300 (of FIGS. 3A through 3D) in a third position according to an embodiment herein. The front member 100 is tilted upon its cylindrical hinge 114 to form an angle of 115 degrees between the first end 102 of the first member 100 and the first end 202 of the back member 200.

FIGS. 6A through 6D illustrate a perspective view, a top view, a side view, and a back view, respectively, of the TLIF implant cage 300 (of FIGS. 3A through 3D) in a fourth position according to an embodiment herein. The front member 100 is tilted upon its cylindrical hinge 114 to form an angle of 90 degrees between the first end 102 of the first member 100 and the first end 202 of the back member 200. Upon reaching the fourth position, the TLIF implant cage 300 is in its final position. The TLIF implant cage 300 may be held in place by the compression of pedicle screws (not shown)

posteriorly. Furthermore, the cage 300 may comprise serrated teeth or a roughened surface on its top and bottom that may assist in preventing extrusion.

The TLIF implant cage 300 may be inserted into the disc space (not shown) after first clearing the residual intervertebral disc (not shown). The surgeon can use trial sizers to determine the appropriate size of the implant cage 300. The surgeon may then pack the implant cage 300 with material used to achieve fusion. This may include local bone or bone graft extenders. The surgeon may then attach the insertion tool (not shown). Preferably, the surgeon will aim the implant cage 300 so that it is inserted in an oblique fashion. The surgeon enters through the excised disc, which are in the lumbar neuroforamen. Once the surgeon feels resistance from the tip of the implant cage 300 meeting resistance, the insertion tool is removed. This releases the front member 100. The surgeon then finishes placing the implant cage 300 by gentle impaction using small footed impactors (not shown). This allows the implant cage 300 to assume its final "V" shape (fourth position, 90 degrees) in the disc space.

Figure 7:
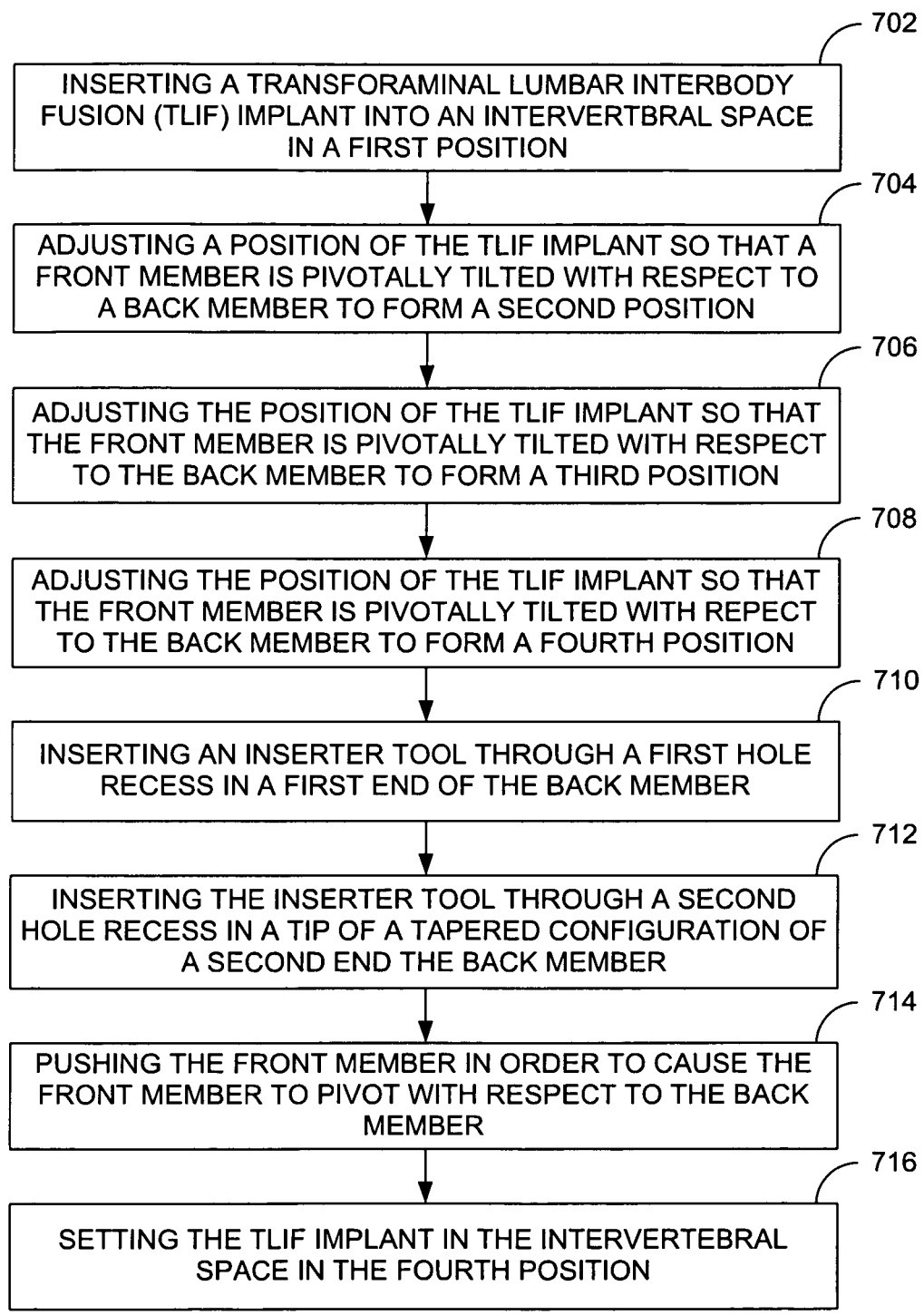
FIG. 7 illustrates a process flow illustrating a method of performing a surgical procedure according to an embodiment herein.

FIG. 7, with reference to FIGS. 1A through 6D, is a process flow diagram illustrating a method of performing a surgical procedure according to an embodiment herein, wherein the method comprises inserting (702) a transforaminal lumbar interbody fusion (TLIF) implant 300 into an intervertebral space in a first position; adjusting (704) a position of the TLIF implant 300 so that a front member 100 is pivotally tilted with respect to a back member 200 to form a second position; adjusting (706) the position of the TLIF implant 300 so that the front member 100 is pivotally tilted with respect to the back member 200 to form a third position; adjusting (708) the position of the TLIF implant 300 so that the front member 100 is pivotally tilted with respect to the back member 200 to form a fourth position; inserting (710) an inserter tool through a second hole recess 246 in a tip of a tapered configuration of a second end 204 of the back member 200; inserting (712) the inserter tool through a first hole recess 218 in a first end 202 of the back member 200; pushing (714) the front member 100 in order to cause the front member 100 to pivot with respect to the back member 200; and setting (716) the TLIF implant 300 in the intervertebral space in the fourth position.

In step 702, the TLIF implant 300 having the front member 100 and the back member 200 is inserted into the intervertebral space (not shown). The front member 100 and the back member 200 are pivotally attached to each other (e.g., through the cylindrical hinge 114, cut out 112 as shown in FIG. 1A through 1D and the attachment head 214, receptor 216 as shown in FIG. 2A though 2D). When inserted into the intervertbral space, the TLIF implant is in a first position. In the first position, the front member 100 is pivoted with respect to the back member 200 to form an angle of zero degree (e.g., as illustrated in FIG. 3A though 3D). In step 704, a position of the TLIF implant 300 is adjusted so that the front member 100 is pivotally tilted with respect to the back member 200 to form a second position. In the second position the front member 100 is pivoted with respect to the back member 200 to form an angle of 45 degrees (e.g., as illustrated in FIG. 4A through 4D). In step 706, the position of the TLIF implant 300 is adjusted so that the front member 100 is pivotally tilted with respect to the back member 200 to form a third position. In the third position, the front member 100 is pivoted with respect to the back member 200 to form an angle of 115 degrees (e.g., as illustrated in FIG. 5A through 5D).

In step 708, the position of the TLIF implant 300 is adjusted so that the front member 100 is pivotally tilted with respect to the back member 200 to form a fourth position. In the fourth position, the front member 100 is pivoted with respect to the back member 200 to form an angle of 90 degrees (e.g., as illustrated in FIG. 6A through 6D). In step 710 the inserter tool (not shown) is inserted through the second hole recess 246 in the tip of the tapered configuration of the second end 204 of the back member 200. In step 712, the inserter tool is inserted through the first hole recess 218 in the first end 202 of the back member 200. In step 714, the front member 100 is pushed in order to cause the front member 100 to pivot with respect to the back member 200. In step 716, the TLIF implant 300 is set in the intervertebral space in the fourth position.

The length of the entire TLIF implant cage 300 is larger than conventional TLIF implants as it includes the front member 100 coupled to the back member 200 and thus provides maximum surface area with excellent post operation pain control secondary to improved stability. Pain control is related to the stability offered by implants. The more stable and the more supportive an implant the less pain after surgery. In this regard, the implant cage 300 offers significant benefit over conventional implants. Furthermore, the implant cage 300 is tilted to form various angles and thus prevents subsidence by maximizing the surface area of the implant cage 300. Accordingly, the implant cage 300 provides maximum surface area by packing more endplate support into the existing disc space.

As mentioned, those skilled in the art have noted that surface area is important to controlling postoperative pain and achieving successful fusion. The embodiments herein use a longer (compared with conventional/traditional devices) interbody implant (spacer) 300 that can collapse as it enters the intervertebral disc space. In doing so the spacer 300 is able to "fold" and achieve much greater endplate support by placing a larger support into a small space. Traditional devices use a 10-12 mm wide spacer. These spacers are often hinged or split allowing them to be inserted as a single unit. Once in the space they are spread, turned, or split so that it then provides 5-6 mm wide support over a longer distance. There is no true change in direct surface area support from the spacer when comparing its expanded and unexpanded state. Conversely, the spacer 300 provided by the embodiments herein provides substantial benefit to patients by folding a larger spacer 300 into the disc space. Rather than dividing a 10-12 mm width spacer that is 22 mm in length as is currently used, the embodiments herein provide the ability to "fold" a much longer spacer that is 10-12 mm wide and up to 40 mm in length. Since the implant 300 is a hinged single unit it also provides substantial benefit over alternative techniques that employ two individual cages that are uncoupled. Furthermore, the embodiments herein, through its superior surface area, limit the risk of subsidence of the spacer 300. Moreover, the embodiments herein also afford immediate postoperative benefit through its larger surface area of support for patients, which may allow patients to return to work and other activities much sooner than traditional surgical techniques. Additionally, the embodiments herein may also provide for an increased fusion rate compared to traditional implants.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A transforaminal lumbar interbody fusion (TLIF) implant to be placed in an intervertebral space, said TLIF implant comprising:
a front member comprising:
a first end comprising a uniformly monolithic cylindrical hinge post;
a second end positioned opposite to said first end and having a tapered configuration;
a pair of lateral portions attached to each of said first end and said second end;
an opening configured through said pair of lateral portions;
a top wall attached to each of said first end, said second end, and said pair of lateral portions;
a bottom wall positioned opposite to said top wall and attached to each of said first end, said second end, and said pair of lateral portions; and
a plurality of openings in each of said top wall and said bottom wall;
a back member pivotally attached to said front member; wherein said back member comprises:
a first end having an arcuately-shaped attachment head comprising a receptor dimensioned and configured to accommodate said hinge of said front member;
a second end positioned opposite to said first end and having a tapered configuration, wherein a tip of said tapered configuration comprises a hole recess;
a pair of lateral portions attached to each of said first end and said second end of said back member;
an opening configured through said pair of lateral portions of said back member;
a top wall attached to each of said first end, said second end, and said pair of lateral portions of said back member;
a bottom wall positioned opposite to said top wall and attached to each of said first end, said second end, and said pair of lateral portions of said back member; and
a plurality of openings in each of said top wall and said bottom wall.

2. The TLIF implant of claim 1, wherein said back member comprises a plurality of slots.

3. The TLIF implant of claim 2, wherein said plurality of slots comprises a top pair of slots in said top wall.

4. The TLIF implant of claim 3, wherein said plurality of slots comprises a bottom pair of slots in said bottom wall.

5. The TLIF implant of claim 4, wherein a rear slot of said top pair of slots in said top wall and a rear slot of said bottom pair of slots in said bottom wall merge.

6. The TLIF implant of claim 1, wherein said first end of said back member comprises a hole recess adjacent to said attachment head of said back member and aligned with the hole recess of said second end of said back member.

7. The TLIF implant of claim 2, wherein said plurality of slots accommodate impactions to turn said TLIF implant.

8. A device for providing intervertebral support, said device comprising:
a first member comprising:
a first end comprising a uniformly cylindrical hinge;
a curved second end positioned opposite to said first end and having a tapered configuration;
a pair of lateral portions attached to each of said first end and said second end, wherein one of the lateral portions comprises an arcuately-shaped cut out region comprising a substantially uniform and flat surface and said hinge;
an opening configured through said pair of lateral portions, wherein a length of said opening is at least equal to half of an overall length of said first member, and wherein said opening is adjacent to said arcuately-shaped cut out region;
a top wall attached to each of said first end, said second end, and said pair of lateral portions;
a bottom wall positioned opposite to said top wall and attached to each of said first end, said second end, and said pair of lateral portions; and
a plurality of elongated openings in each of said top wall and said bottom wall, wherein the openings in said top wall are aligned with the openings in said bottom wall;
a second member pivotally attached to said first member; wherein said second member comprises:
a first end having an arcuately-shaped attachment head corresponding to said arcuately-shaped cut out region of said first member, wherein said attachment head comprises a receptor dimensioned and configured to pivotally attach to said hinge of said first member;
a second end positioned opposite to said first end and having a tapered configuration, wherein a tip of said tapered configuration comprises a hole recess positioned parallel to a longitudinal axis of said second member;
a first lateral portion attached to each of said first end and said second end of said second member;
a second lateral portion positioned opposite to said first lateral portion and attached to each of said first end and said second end of said second member;
an opening configured through said first lateral portion and said second lateral portion of said second member;
a top wall attached to each of said first end, said second end, said first lateral portion and said second lateral portion of said second member;
a bottom wall positioned opposite to said top wall and attached to each of said first end, said second end, said first lateral portion and said second lateral portion of said second member; and
a plurality of openings in each of said top wall and said bottom wall, wherein said openings in said top wall are aligned with said openings in said bottom wall,
wherein a first lateral side of said attachment head is offset from an edge of said first lateral portion of said second member, and
wherein a second lateral side of said attachment head is planar with an edge of said second lateral portion of said second member.

9. The device of claim 8, wherein said second member comprises a plurality of slots.

10. The device of claim 9, wherein said plurality of slots comprises a top pair of slots in said top wall and a bottom pair of slots in said bottom wall.

11. The device of claim 10, wherein a rear slot of said top pair of slots in said top wall and a rear slot of said bottom pair of slots in said bottom wall merge.

12. The device of claim 11, wherein said first end of said second member comprises a hole recess adjacent to said attachment head of said second member and aligned with the hole recess of said second end of said second member.

13. The device of claim 8, wherein said plurality of slots accommodate impactions to turn said device.

14. A device for providing intervertebral support, said device comprising:
   a first member comprising:
      a first end comprising a monolithic cylindrical hinge;
      a curved second end positioned opposite to said first end and having a tapered configuration;
      a pair of lateral portions attached to each of said first end and said second end, wherein one of the lateral portions comprises an arcuately-shaped cut out region comprising said hinge;
      an opening configured through said pair of lateral portions, wherein a length of said opening is at least equal to half of an overall length of said first member, and wherein said opening is adjacent to said arcuately-shaped cut out region;
      a top wall attached to each of said first end, said second end, and said pair of lateral portions;
      a bottom wall positioned opposite to said top wall and attached to each of said first end, said second end, and said pair of lateral portions; and
      a plurality of elongated openings in each of said top wall and said bottom wall, wherein the openings in said top wall are aligned with the openings in said bottom wall;
   a second member pivotally attached to said first member; wherein said second member comprises:
      a first end having an arcuately-shaped attachment head corresponding to said arcuately-shaped cut out region of said first member, wherein said attachment head comprises a receptor dimensioned and configured to pivotally attach to said hinge of said first member;
      a second end positioned opposite to said first end and having a tapered configuration, wherein a tip of said tapered configuration comprises a hole recess positioned parallel to a longitudinal axis of said second member;
      a first lateral portion attached to each of said first end and said second end of said second member;
      a second lateral portion positioned opposite to said first lateral portion and attached to each of said first end and said second end of said second member;
      an opening configured through said first lateral portion and said second lateral portion of said second member;
      a top wall attached to each of said first end, said second end, said first lateral portion and said second lateral portion of said second member;
      a bottom wall positioned opposite to said top wall and attached to each of said first end, said second end, said first lateral portion and said second lateral portion of said second member; and
      a plurality of openings in each of said top wall and said bottom wall, wherein said openings in said top wall are aligned with said openings in said bottom wall,
      wherein a first lateral side of said attachment head is offset from an edge of said first lateral portion of said second member,
      wherein a second lateral side of said attachment head is planar with an edge of said second lateral portion of said second member, and
      wherein said first end of said second member comprises a hole recess adjacent to said attachment head of said second member and aligned with the hole recess of said second end of said second member.

15. The device of claim 14, wherein said second member comprises a plurality of slots.

16. The device of claim 15, wherein said plurality of slots comprises a top pair of slots in said top wall and a bottom pair of slots in said bottom wall.

17. The device of claim 16, wherein a rear slot of said top pair of slots in said top wall and a rear slot of said bottom pair of slots in said bottom wall merge.

18. The device of claim 15, wherein said plurality of slots accommodate impactions to turn said device.

19. The device of claim 14, wherein an inserter tool is inserted through said hole recess of said second end of said second member.

20. The device of claim 14, wherein an inserter tool is inserted through said hole recess of said first end of said second member.

* * * * *